(12) United States Patent
Benner (10) Patent No.: US 8,034,563 B1
(45) Date of Patent: Oct. 11, 2011

(54) ACTIVATED JOINING OF NUCLEIC ACID PROBES

(76) Inventor: Steven Albert Benner, Gainesville, FL (US)

( * ) Notice: Subject to any disclaimer, the term of this patent is extended or adjusted under 35 U.S.C. 154(b) by 0 days.

(21) Appl. No.: 11/519,265

(22) Filed: Sep. 12, 2006

(51) Int. Cl.
*C12Q 1/68* (2006.01)
(52) U.S. Cl. .......................................... 435/6.1
(58) Field of Classification Search ............. 435/6.1
See application file for complete search history.

(56) References Cited

U.S. PATENT DOCUMENTS

| | | | | |
|---|---|---|---|---|
| 5,780,234 | A * | 7/1998 | Meade et al. ........... | 435/6 |
| 2003/0129611 | A1 * | 7/2003 | Bao et al. .............. | 435/6 |
| 2004/0180412 | A1 * | 9/2004 | Liu et al. .............. | 435/91.2 |

OTHER PUBLICATIONS

Masuko et al. Nucleic acids Research, vol. 26, No. 23, pp. 5409-5416, 1998.*
Ihara et al. Nucleic Acids Symposium Series No. 48, pp. 125-126, 2004.*
Chang et al. Helvetica Chimica Acta, vol. 80, pp. 1106-1121, 1997.*
Malakhov et al. Eur. J. Org. Chem, vol. 2004, issue 6, pp. 1298-1307, 2004.*
Fujimoto et al., J. Am Chem. Soc. vol. 5, pp. 5646-5647, 2000.*

* cited by examiner

*Primary Examiner* — Gary Benzion
*Assistant Examiner* — Cynthia Wilder (57) ABSTRACT

A process is provided to generate fluorescent molecules in the presence of target nucleic acids, but not in the absence of that target. Two probes, one bearing moiety A and the other bearing moiety B, bind to the target in a way that brings A and B together. A photon then converts A into A*, which can react with B to form a new species Z that is fluorescent. If A* does not encounter B, then A* reverts to form A. This allows the probe to have another opportunity to be activated should it be later bound near B. In one embodiment, a photoenolization creates A* as a diene; this reacts with a dienophile B in a Diels-Alder reaction. The linker Z may cause the linked probes to bind less tightly to the target, allowing the target to generate many fluorescent products, or be read through by a polymerase.

16 Claims, 9 Drawing Sheets

ACTIVATED JOINING OF NUCLEIC ACID PROBES

FIELD

This invention relates to the field of nucleic acid chemistry, more specifically to the field of compositions and processes that can be used to detect nucleic acid analogs. Most specifically, this invention relates to a process, and compositions for enabling that process, for detecting nucleic acids by a reaction that joins two probe molecules together covalently when they are held in proximity by the analyte oligonucleotides molecule that is being detected.

BACKGROUND

A major objective of bioanalytical chemistry is to detect small amounts of DNA or RNA in samples. These samples are, of course, routinely found in research laboratories. However, they are also found in the clinic, where they can be obtained from human patients, or in veterinary medicine, where they come from animals, or in public places (such as a post office), where they might indicate the presence of an infectious disease, or on the battlefield, where they might indicate that an adversary is using a biological warfare agent. As one moves farther from the research laboratory, the desired specifications become more demanding:

1. Sensitivity. The ultimate goal is to detect single molecules of the analyte nucleic acid, preferably without needing to amplify it (as is presently done using the polymerase chain reaction).
2. Selectivity. The ultimate goal is to detect the analyte in complex biological material, including an environment that may contain billions of other oligonucleotide sequences.
3. Cost. A cheaper analytical tool is nearly always preferable to a more expensive tool.
4. Convenience. Ideally, detection should be done in a single step.
5. Readout. The readout must be simple, recognizing that simplicity is defined in many cases by the goal. On the battlefield, for example, a visual readout is desirable. In a trap seeking the Hanta virus in rodents, for example, an electrical readout might be desired.
6. Multiplexing. It is often desirable to be able to detect multiple oligonucleotide analytes at the same time.
7. Time. A read-out in seconds or minutes is preferable to read-outs that require more time to obtain.
8. Sample preparation. None is generally desirable.
9. Reproducibility is preferably be high; false positives are preferably low.
10. Dynamic range. The ability to quantitate from a single molecule to hundreds of thousands has value in specific circumstances.

The binding of DNA, RNA and DNA analogs (collectively called "probes") to targeted natural DNA and RNA (called the "analyte" molecules, herein referred to as "N") offers a step in a process that might be used to detect natural analyte molecules and, thereby, might support an assay that infers the presence of the living system that carries that analyte. Probes have been used for 40 years for this purpose, with their use accelerating as synthetic DNA became readily available in the early 1980's.

A variety of architectures are available to exploit the binding of analyte molecule to a probe molecule to generate a detectable readout as a consequence of that binding. These can be classified in various ways. One classification counts the number of probe molecules that are used in the assay. Thus, many architectures for detecting DNA sequences use a single probe molecule. Another class of architectures, however, uses the binding between an analyte and two probe molecules to generate the readout. Here, the most common feature allows the analyte molecule to bring the two probe molecules together in space. Once so arranged, the proximity between the two probes is then used as the basis for the generation of the read-out.

One well known example of this architecture is the "binary beacon". Here, one of the two probes brought into proximity carries a fluorescence energy donor, while the second carries a fluorescence energy acceptor. Only when the two are held in proximity by hybridization to the analyte is fluorescent resonant energy transferred efficiently between the two. This process was demonstrated some time ago by Cardullo et al. [Car88] in vitro (see also review by [Tsi93]). Tsuji et al. used the FRET strategy to observe human c-fos mRNA inside a living transfected Cos7 cell [Tsu01]. With the efficiency of fluorescent resonance energy dropping with the sixth power of the distance between the energy donor and the energy acceptor, close proximity effected by having both molecules bind to the probe is an important contributor to the efficiency.

This work also illustrated many reasons why this analytical task is difficult. First, the secondary structure of an mRNA (if this is the analyte) itself is problematic. These workers identified by experiment a 40 mer sequence that hybridized with high efficiency to probes 15-20 nucleotides in length. To prevent the tagged DNA probes from accumulating in the nucleus, they bound them to streptavidin, which allowed them to be stable in the cytoplasm for over 30 minutes. This is, of course, a problem general to any method that hopes to detect an analyte by exploiting a probe.

Other issues relate to the sensitivity of this approach. Even without resonant energy transfer, a small amount of fluorescence is generally created by the second fluor even if the excitation wavelength is not optimally suited for direct excitation. This creates background noise. Thus, Tsuji et al. microinjected approximately $10^5$ molecules into the cells that they studied, and were able to detect a specific mRNA only if it was present at ca. 10,000 copies of per cell [Tsu01]. They noted that both the fluorescence of the unhybridized fluorescent molecules introduced into the cell, as well as background autofluorescence of components naturally in the cell, limited the signal-to-noise ratio that might be achieved by this approach. They noted that the latter might be reduced by examining fluorescence species that absorb and emit at longer wavelengths. To seek the FRET signal above the noise arising from unhybridized fluroescent probes, Tsuji et al. also explored time-resolved fluorescence spectroscopy [Tsu01].

Fluorescence readout is not the only way to generate a read-out as a consequence of the binding of two probes in adjacent positions on an analyte molecule. For example, such binding might lead to the formation of a covalent bond between the two probe molecules. Examples of this process have been available for over 20 years [Kie86]. More recently, Xu and Kool [Xu97] replaced the 5'-hydroxyl group on a DNA fragment by an iodo group on the 5'-end of one probe, and placed a phosphorothioate on the 3'-end of the second probe. Binding the two to an analyte molecule N on adjacent segments of the oligonucleotides sequence brought the reactive electrophilic center (the carbon attached to the iodine) into proximity to the reactive nucleophilic center, and facilitated their reaction to make a covalent phosphothioate diester bond. Here, the reaction is faster because the two species having complementary reactivity are held together by hybridization to the analyte.

While in widespread use, such strategies suffer from the intrinsic background reaction between nucleophile and electrophile as they come into contact in the absence of the analyte molecule. This renders most of the architectures laboratory curiosities.

As recently as 2002, various groups have attempted to carve out intellectual property from this basic idea. For example, Liu, Gartner and Calderone (United States Patent Application 20040180412) have claimed a method of inducing reaction between first and second reactive units attached to oligonucleotides probes by using a nucleic acid-templated chemical reaction. Their method comprised the steps of: (a) providing (i) a template comprising a first reactive unit associated with a first oligonucleotide comprising a codon and (ii) a transfer unit comprising a second reactive unit associated with a second oligonucleotide comprising an anti-codon capable of annealing to said codon, wherein said codon or said anti-codon comprise first and second spaced apart regions; (b) annealing said oligonucleotides together thereby to bring said first reactive unit and said second reaction unit into reactive proximity, wherein said codon or said anti-codon having said first and second spaced apart regions produce a loop of oligonucleotides not annealed to the corresponding anti-codon or codon; and (c) inducing a covalent bond-forming reaction between said reactive units to produce a reaction product. This was proposed to be a tool for generating libraries of organic molecules for the purpose of chemical screening.

A consideration of thermodynamics provides a theoretical perspective on such approaches, insight into why they will not have high utility as they are presently implemented, and ideas for alternative implementations that are more likely to be useful. First, if the untemplated joining of two molecules is to be avoided, energy that drives (either from a kinetic or a thermodynamic perspective) the ligation reaction cannot be intrinsically present in the reactive species at the ends of the probes. Rather, this energy must be introduced from time to time to create an activated probe ready to form a covalent bond with the capture probe, and then be dissipated. The rate of energy dissipation must be slow enough to allow the formation of the desired covalent link between the two probe molecules if they are preorganized, held together by binding to the analyte. If they are not pre-organized, however, however, the energy must be dissipated before the activated probe molecule finds its reaction partner by diffusion in solution. This can be had by having the activated moiety react harmlessly with bulk assay components (for example, the water in the assay).

Further, the architecture is most effectively implemented if the dissipation restores the activated probe to a state identical to that before activation. This conserves the probe, allowing it to have another opportunity to be activated again in the future, when it is possibly bound near its capture probe to an analyte molecule.

This activation can, of course, come from adding a chemical reagent. Several of these are contemplated in the invention described below. The preferred implementation of this strategy, however, is use of a photon to activate an activatable moiety on one of the probes.

DESCRIPTION OF THE INVENTION

The basic strategy involves two moieties, referred to here as "A" and "B" that are attached to the 3'- and 5'-ends (respectively) of a 5'-terminal binding fragment and a 3'-terminal binding fragment (respectively), where the sequences of these two fragments are chosen to bind adjacently on a preselected target analyte and thereby bring A and B into close proximity. The A and B moieties are unreactive. Introduction of energy after the two fragments have had the opportunity to bind to the analyte transforms one of the two (in this example, A) into a species (A*) that has a new reactivity that enables it to react with B to form a new covalent bond that links the backbone.

There is no requirement that the A and B units be placed on the 3'- and 5'-ends (respectively) of a 5'-terminal binding fragment and a 3'-terminal binding fragment (respectively). The essence of the invention is not changed if the A and B moieties are placed at the 5'- and 3'-ends (respectively) of the 3'-terminal binding fragment and the 5'-terminal binding fragment (respectively).

Figure 1:
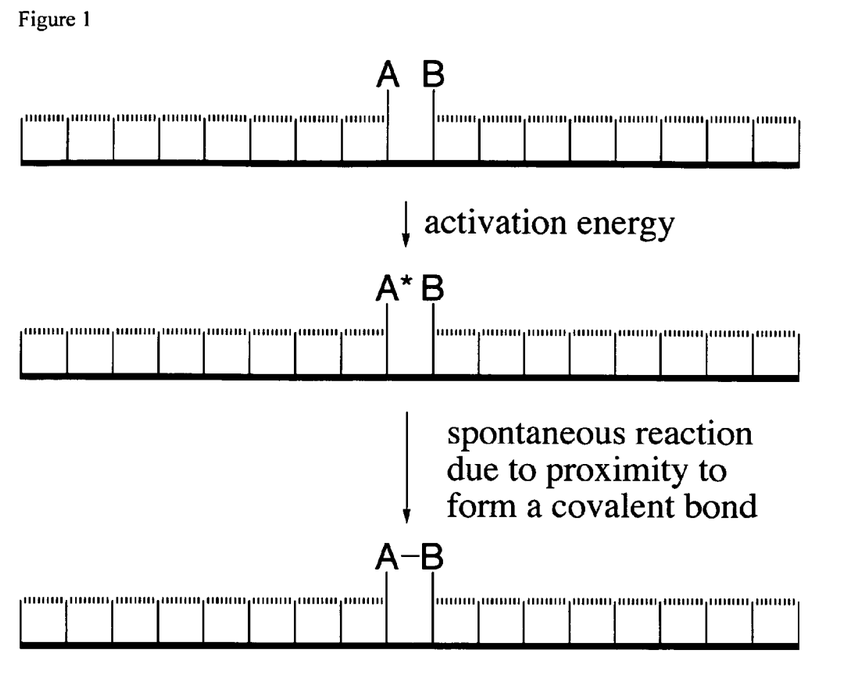
FIG. 1. The essential elements of the instant invention are the presence of two moieties, referred to here as "A" and "B", at the 3'- and 5'-ends (respectively) of a 5'-terminal binding fragment and a 3'-terminal binding fragment (respectively), where the sequences of these two fragments are chosen to bind adjacently on a preselected target analyte and thereby bring A and B into close proximity. The A and B moieties are unreactive. Introduction of energy after they have had the opportunity to bind to the analyte transforms one of the two (in this example, A) into a species (A*) that has a new reactivity that enables it to react with B to form a new covalent bond that links the backbone.
Figure 2:
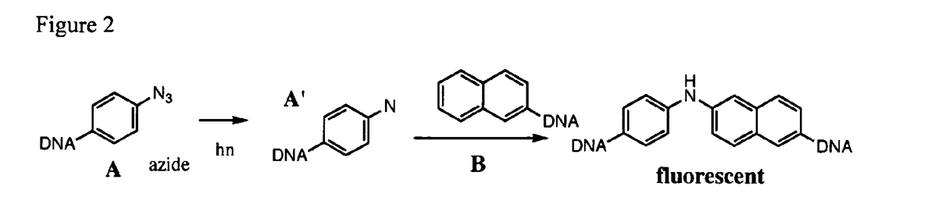
FIG. 2. An example of specific implementation of the instant invention where the conversion of A to A* is irreversible, and involves the formation of a fluorescent product Z.

Many A:B pairs meet these specifications. For example, FIG. 2 shows an implementation of the architecture where the conversion of A to A* is irreversible. The species that is generated is a nitrene, which is highly reactive. The product that is generated when the nitrene reacts with a naphthalene B moiety to make a fluorescent product, a phenyl naphthylamine. If the nitrene intermediate does not rapidly find its partner B, it reacts intramolecularly or harmlessly with solution components, thus dissipating the energy. A variety of other implementations are described below.

The preferred embodiments are distinct in the nature of the linkage that is created by the reaction between A* and B. In one class of embodiments, the product of the reaction is fluorescent, as is the case in FIG. 2. The fluorescent product generates a readout upon irradiation with the correct fluorescent light that is a direct consequence of the presence of the analyte. This fluorescent establishes the presence of the analyte molecule in the assay mixture.

In another class of embodiments, the product of the reaction between A* and B causes sufficient distortion of the duplex structure that the linked probe molecules bind less tightly to the analyte than do the monomeric probe molecules. Extensive studies in the Benner group over the past decade (summarized in [Ben04][Hut02]) have shown that such linkers often destabilize the duplex. This is the case for the linker generated in the example shown in FIG. 2. In these cases, after the covalent bond is formed, the two probes, now joined, will dissociate from the mRNA target analyte. This allows the analyte to be "catalytic", generating many liganded species from a single analyte molecule. If the product is also fluorescent, multiple fluorescent molecules will be generated from a single analyte molecule. This has obvious advantages for enhancing signal to detect analyte molecules in small amounts.

In a third class of embodiments, the product of the reaction between A* and B is a linker that, although unnatural, can be read through by a polymerase to give a natural complementary strand. This is a case with the example shown in FIG. 5. If the linker can be read through, the linked probe pair may serve as a template for further polymerase reactions. This is advantageous for still other applications.

Figure 3:
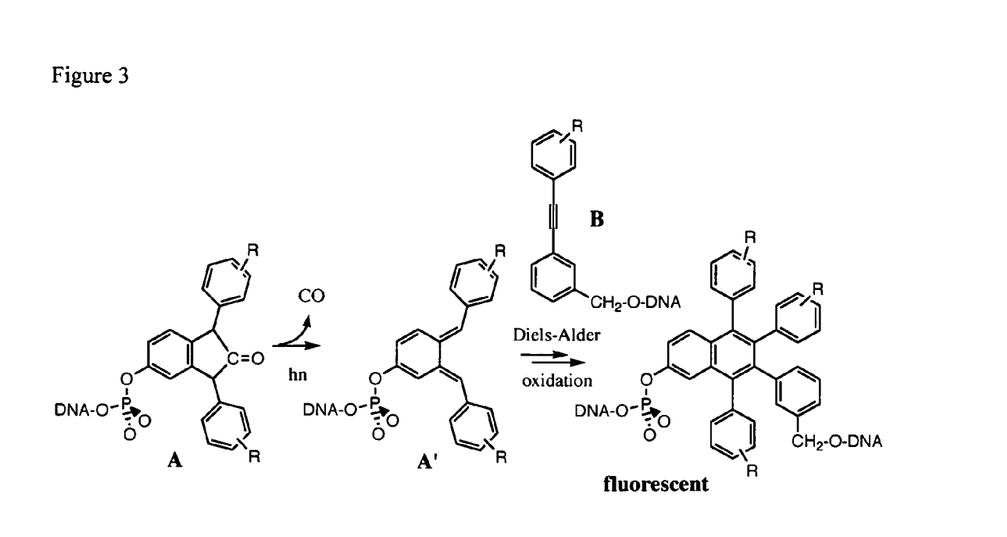
FIG. 3. An example of specific implementation of the instant invention where the conversion of A to A* is irreversible, and the covalent bond formation involves a Diels-Alder reaction.
Figure 4:
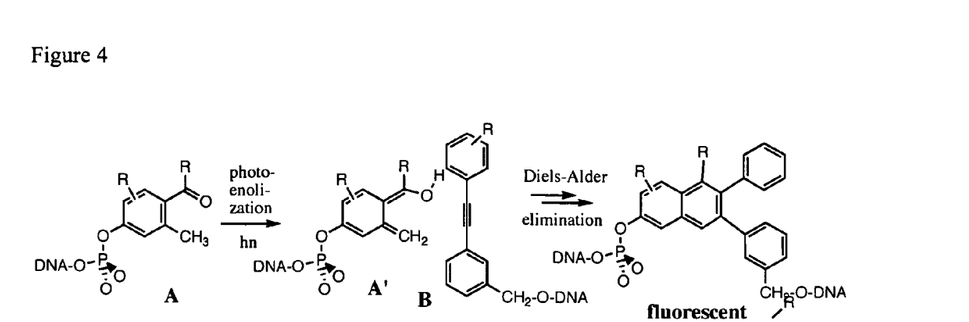
FIG. 4. An example of specific implementation of the instant invention where the conversion of A to A* is reversible, a photoenolization where the photoenol generates a diene that, if it does not encounter a dienophile, reverts to the starting material.

Several other chemistries are shown in FIGS. 3 and 4. In particular, two embodiments are presented where a Diels-Alder reaction forms the covalent bond. In the first, the diene is formed through the photoextrusion of carbon monoxide. This is an irreversible process.

The second implementation of a process of the instant invention that uses a Diels-Alder reaction to generate the covalent bond generates a diene upon photoirradiation. Photoenolization with 2-methylbenzophenones was reported by Yang in 1961 [Yan61]. It proceeds via a radical mechanism, and is especially effective with benzophenone structures. The overall quantum yields is typically 0.5. The resulting diene does not have the high reactivity of other photoproducts. If it does not encounter a dienophile B on its partner probe, it will simply ketonize to give the starting benzophenone species. This means that a single probe molecule can have an indefinite number of opportunities to find its target.

This particular embodiment of the instant invention shows many of the advantages of a binary probe process that is designed following the full thermodynamic analysis. Here, a photoenolization reaction of a 2-methyl aromatic ketone uses the energy of an incoming photon to create an enol diene on one probe molecule. The diene reacts in a Diels-Alder reaction with a dienophile on the second probe molecule, if the two are held adjacent on an analyte. Should the activated diene not quickly encounter the dienophile via adjacent binding, the enol tautomerizes to restore the a 2-methyl aromatic ketone, which has the opportunity to later photoenolize when, perhaps, analyte is present.

The absorbance spectra for the photoinduced reaction can be adjusted by changing substitutents to be suited for a specific application. As is well known in the art, adding functionality in conjugation with the photoreactive chromophore shifts the optimal wavelength for the photoexcitation to the red. Likewise, changing of substituents in this fashion will shift the emission towards the red. Whether or not this is desirable depends on the specific application. For example, a shift towards the red may be desired when using the probes inside the cell to avoid the autofluorescence of the cell.

Alternative Chemical Implementations

We now disclose a variety of different implementations of this process where chemistries are adapted to different demands imposed by different applications.

Detecting mRNA Molecules Inside of Neurons

A specific chemical implementation of the instant invention is the "light activated fluorescent reporter" (LAFR) strategy for detecting mRNA inside a cell. Here, a reagent cannot be added to the complex between molecule X and molecule Y, as it is inside a cell. Therefore, the reaction converting A to A* must be photochemical. Further, the probe molecules, once joined inside the cell, can conveniently report that the joining has occurred only through the emission of a photon. Therefore, the presently preferred embodiment is one where the product molecule Z is fluorescent. Further, the probes must compete in their binding to mRNA with mRNA secondary structure, and with the binding to RNA binding proteins within the cell. They might themselves bind to RNA binding proteins in the cell. Further, simple DNA molecules and RNA molecules, if they are used as probes, may be degraded in the cell too rapidly for utility. Therefore, the presently preferred implementation does not use a DNA or RNA backbone, but rather uses a 2'-OMe RNA backbone or, more preferably, such a backbone where alternate nucleic acids are replaced by the locked nucleic acid analogs of Imanishi and Wengel.

Detecting Nucleic Acids in Solutions that are Exposed to the Environment

In many assays, it is desirable to have the assay medium be in contact with the general environment, including the atmosphere. These assays might, for example, detect nucleic acids in a post office or a battlefield that come from biohazards and infectious agents. This creates problems for processes that involve the contact between analytes and probes that are use purely aqueous media. Here, while buffers, antioxidants, and salts may be present, and indeed are nearly always used in any practical process of the type disclosed here, water is the principal component. Water, of course, evaporates from assay mixtures when exposed to environments that have less than 100% relative humidity. For certain applications, for example when attempting to detect infectious agents that might be used in biological warfare or in bioterrorism, the humidity of the atmosphere can be significantly lower than this, and even as low as 10%.

Therefore, to implement the instant inventions in these environments, this invention provides for assays to occur in mixtures of water and formamide. Formamide is generally regarded as a denaturant for duplex formation, meaning that hitherto in the art there seems to be no teaching that formamide should be used in such assays. Thus, this teaching is novel and inventive here, as it is new, useful, and enabled.

The enablement is captured in the data below. Here, it is shown that while DNA-DNA duplexes do not remain at high concentrations of formamide, duplexes with RNA (shown in the Table), duplexes with 2'-OMe RNA, and duplexes that contain significant fractions of LNA are all stable in high concentrations of formamide. As a 43% humidity atmosphere (obtained over a saturated solution of potassium carbonate, for example) is in equilibrium with a 30:70 water:formamide liquid phase, this provides a lower limit on the utility of this process with simple RNA probes.

| Pair | % formamide | Tm | Pair | % formamide | Tm |
|---|---|---|---|---|---|
| DNA-DNA | 0 | 61 | DNA-DNA | 50 | 28 |
| DNA-RNA | 0 | 58 | DNA-RNA | 50 | 29 |
| RNA-DNA | 0 | 62 | RNA-DNA | 50 | 31 |

-continued

| Pair | % formamide | Tm | Pair | % formamide | Tm |
|---|---|---|---|---|---|
| RNA-RNA | 0 | 73 | RNA-RNA | 50 | 48 |
| DNA-DNA | 25 | 44 | DNA-DNA | 70 | <20 |
| DNA-RNA | 25 | 42 | RNA-RNA | 70 | 40 |
| RNA-DNA | 25 | 45 | | | |
| RNA-RNA | 25 | 60 | RNA-RNA | 90 | <25 |

DNA: 5'-CTT CAG GTA CTG AGT CAA GC-3'; 5'-GCT TGA CTC AGT ACC TGA AG-3'
RNA: 5'-CUU CAG GUA CUG AGU CAA GC-3'; 5'-GCU UGA CUC AGU ACC UGA AG-3'

An additional advantage of running this reaction in this denaturing medium is that it allows for assay medium and probe combinations that permit cells containing analyte nucleic acids to be disrupted in the same medium as the binding between probe and analyte occurs. The invention also provides assay media, probe combinations, and processes that permit the detection of analyte-probe combinations in the same mixture that the cell is disrupted and the analyte binds the probe.

Elaborating, while the binding of DNA and DNA analogs ("probes") to natural DNA and RNA (the "analyte" molecules) offers a step in a process that detects natural analytes and, thereby supports an assay that infers the presence of the living system that carries that DNA. That process is useful only if the analyte and probe molecules can contact each other. Frequently, the analyte molecules are not easily accessible to the probes, as the analytes are inside cells, cell walls, spores, nuclei, or other biological structures (called, collectively, the "cell") while the probe molecules are outside. In many applications to detect analytes, therefore, significant effort must be expended to prepare the sample before the binding process can begin. Indeed, sample preparation can constitute a significant, or even predominant, part of an assay, and can contribute significantly to its cost.

For this reason, compositions of matter that allow the disruption of the cell in a way that allows probe molecules outside of the cell to contact analyte molecules previously inside the cell under the same conditions as the probe and analyte molecules bind to each other, would be useful. Still more useful would be compositions of matter that allow the disruption of the cell in a way that allows probe molecules outside of the cell to contact analyte molecules previously inside the cell under the same conditions as the probe and analyte molecules bind to each other, and under the same conditions as the binding between probe and analyte molecules is detected as part of the assay. For this purpose, the probes have every third nucleotide position substituted by LNA. Hybridization is carried out in 50% formamide, 0.5% SDS, 5×SSPE, and 5×Denhardt's solution at 34-45° C.

Assembling a Template that can be Read Through

Figure 8:
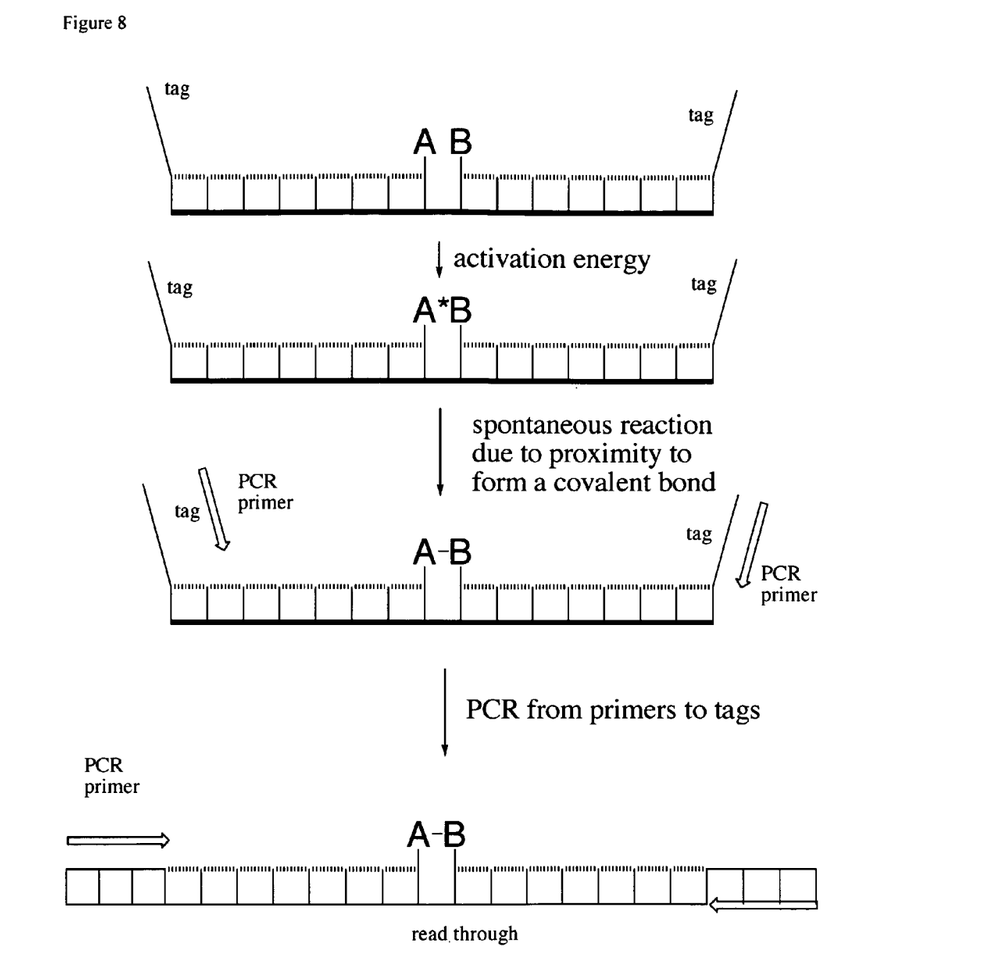
FIG. 8. Architecture where the joining reaction leads to tagged PCR amplification.
Figure 9:
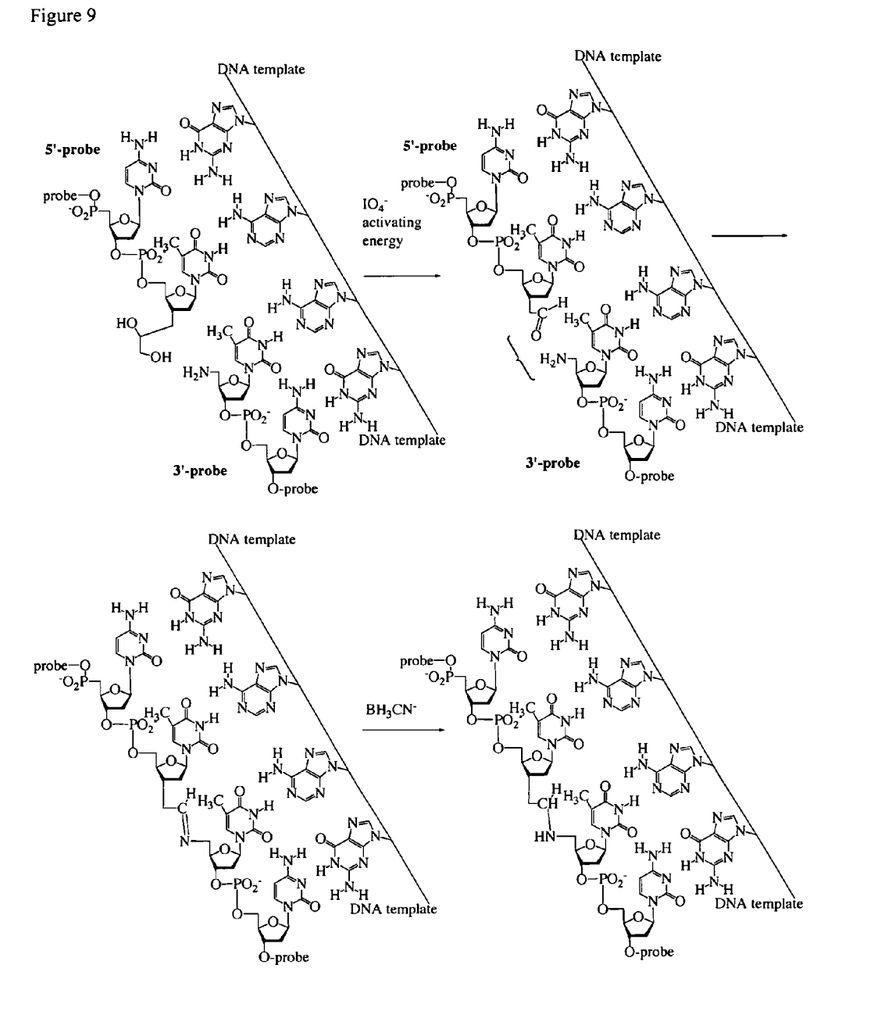
FIG. 9. Implementation where periodate serves as an activating reagent.

Simple architectures can be envisioned for amplifying a signal from a nucleic acid analyte N that involve PCR amplification as shown in FIG. 8, where the joining reaction creates a linker that can be read through by a polymerase. Many artificial linkers can be read through by many DNA polymerases; indeed, it is difficult to prevent a polymerase from reading through many unnatural linkers to some degree. In this architecture, constraints imposed by a goal of intracellular detection or detection in the environment are not present. Reagents can be added to activate the A moiety to make it A* prior to the addition of the polymerase. FIG. 9 shows some chemistry that implements this. Here, the activating reagent is periodate, acting on a 5'-probe that has a diol at its 3'-end, and a 3'-probe that has a 5'-amino-5'-deoxyribose at its 5'-end. The resulting activation is irreversible, and creates an imine linkage that, upon treatment with borohydride, can be read through.

Figure 5:
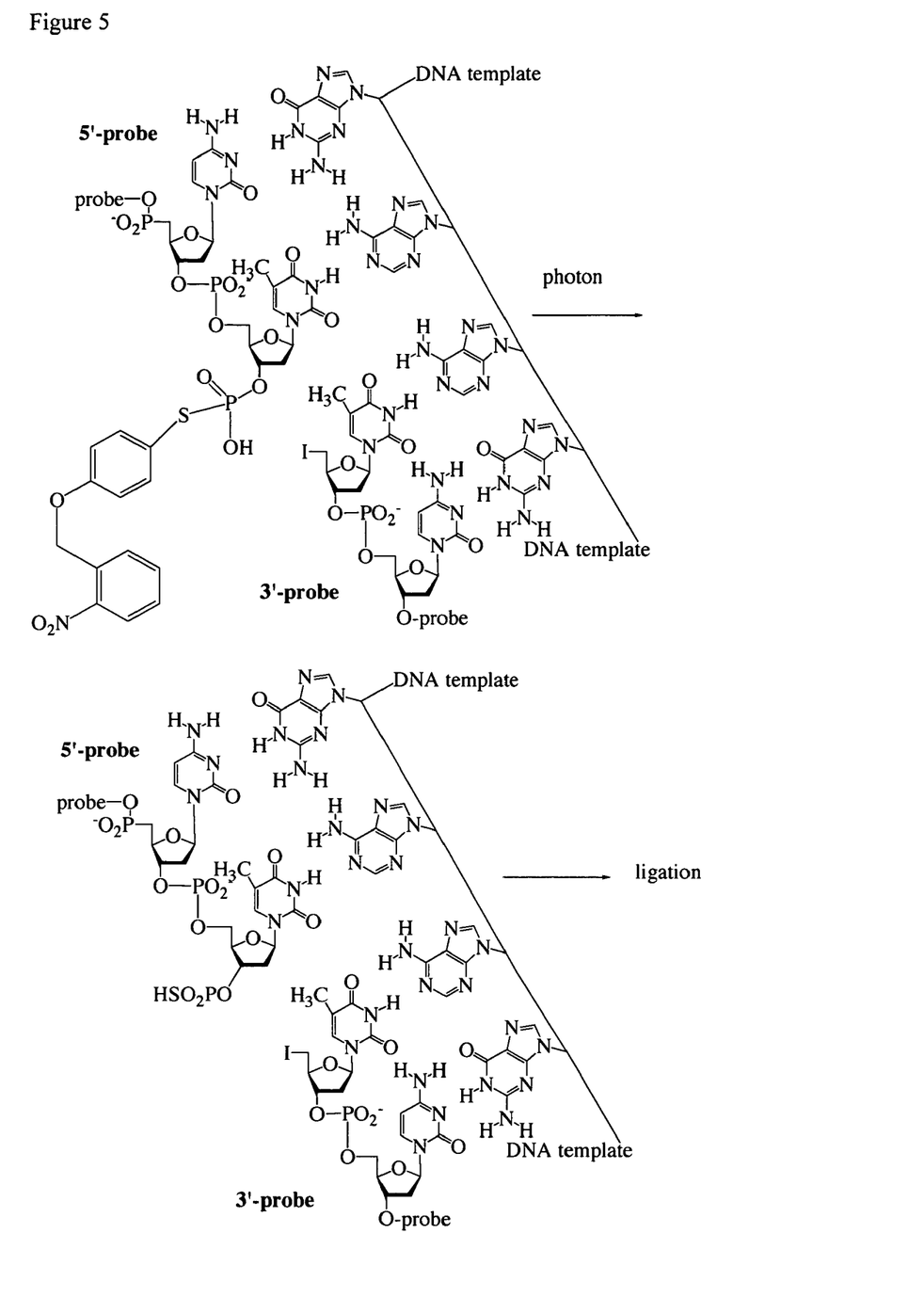
FIG. 5. An example of specific implementation of the instant invention where the conversion of A to A* is irreversible, and where the resulting covalent bond can be read through by a DNA or RNA polymerase.
Figure 6:
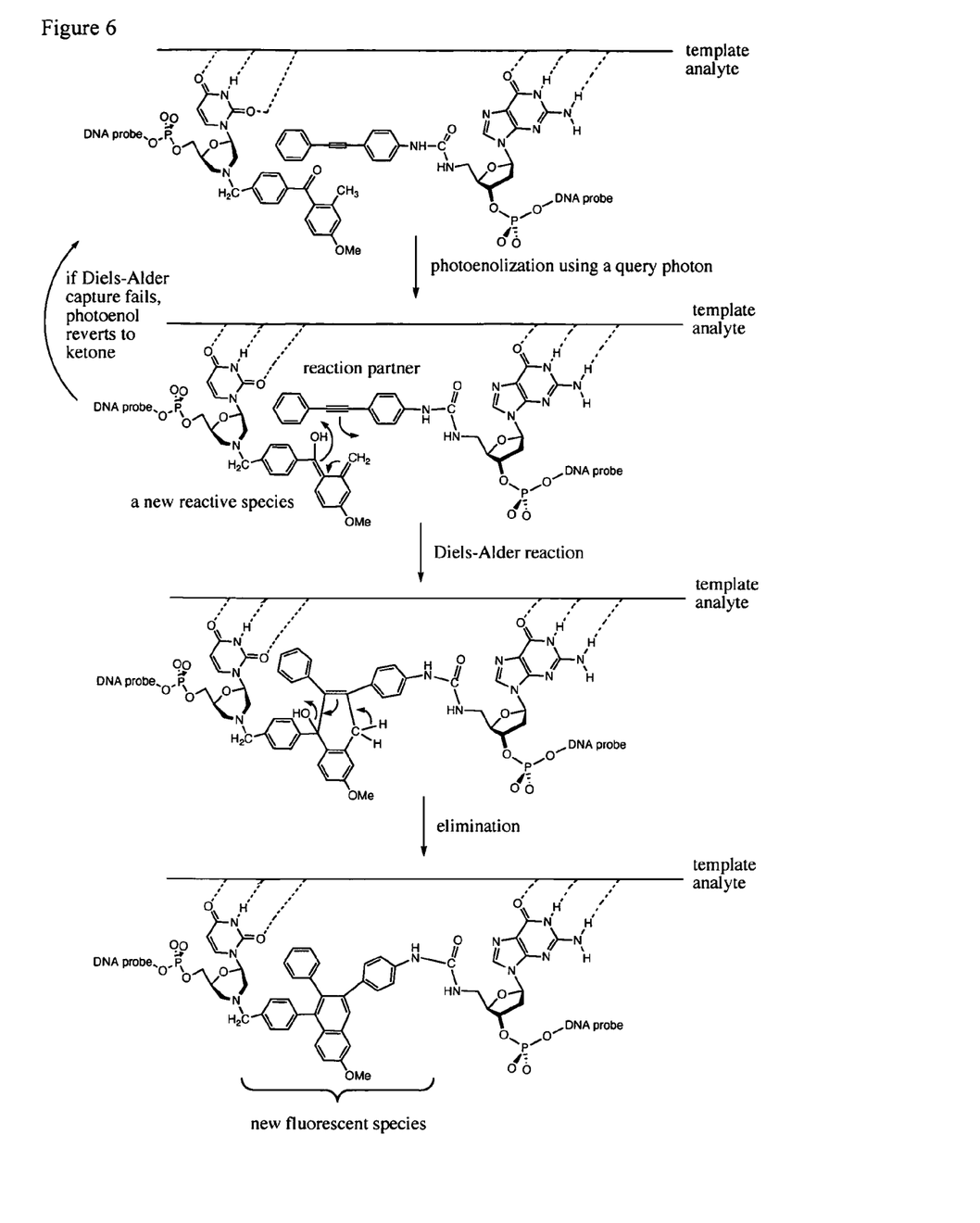
FIG. 6. A schematic in greater detail involving a reversible photoenolization.
Figure 7:
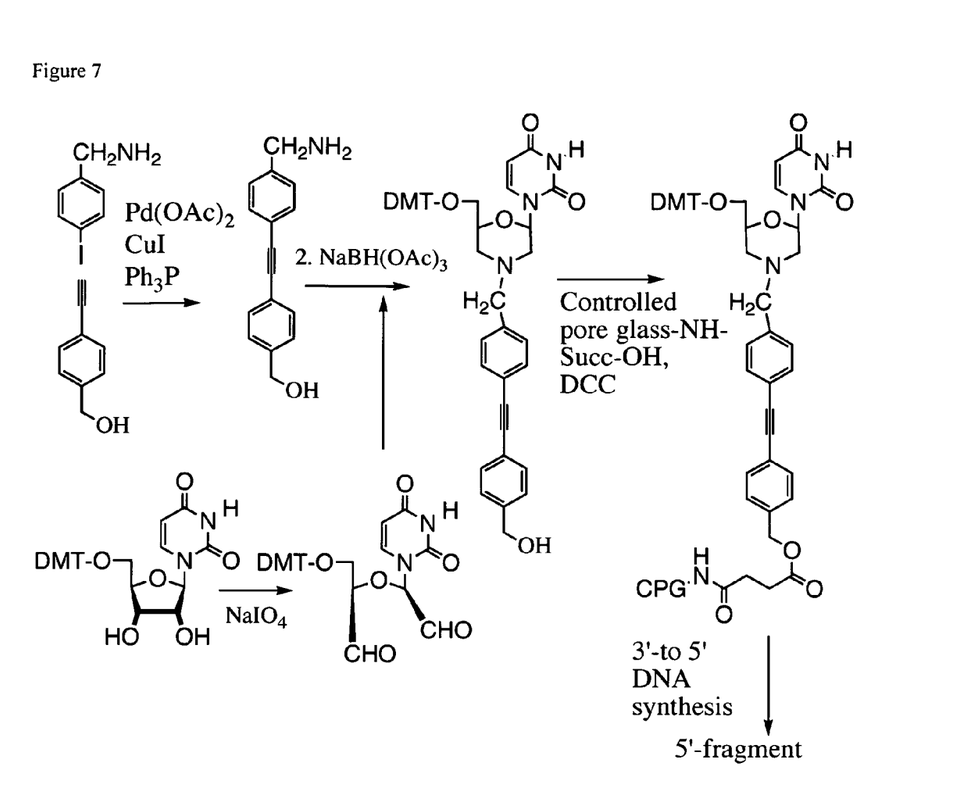
FIG. 7. Synthesis of the dienophile for the reversible photoenolization architecture.

An alternative implementation is shown in FIG. 5. Here, the reagent removes a protecting group from the sulfur of a 3'-phosphorothioate, creating an active nucleophile at the 3'-end of the 5'-fragment. The 5'-end of the 3'-fragment is a 5'-iodo-5'-deoxynucleoside. After deprotection, a ligation of the type described by Xu and Kool can take place. This leads to a phosphorothioate linkage that is read through by most polymerases.

With this architecture, it is possible to do the PCR amplification with tags that are attached to the probes that need not be complementary to the analyte. The presently preferred implementation incorporates elements of an artificially expanded genetic information system, described by Benner [Ben04]. This permits the primers present in high abundance not to cross-react with other nucleic acids in a biological mixture, which is normally quite complex.

Example 1

Preparation of the Probe Containing a Dienophile 4-(4-hydroxymethylphenylethynyl)benzylamine: A mixture of 4-iodo-(aminomethyl)-benzene (7.4 mmol), palladium acetate (0.015 mmol), triphenylphosphine (0.18 mmol), and CuI (0.18 mmol) in anhydrous THF (40 mL) is thoroughly degassed by purging under Ar. To this solution under Ar is added 4-hydroxymethylphenylacetylene (7.4 mmol) and $Et_3N$ (11 mmol). The mixture was then incubated at RT with stirring overnight. The mixture is diluted with EtOAc (150 mL) and the solids are removed by filtration through Celite. The crude residue obtained from the filtrate is purified by flash column chromatography (silica, 1:1 hexane:$Et_2O$) to give the product as a slightly yellow solid.

A variety of substituted phenylacetylenes and iodo compounds can be used. The phenylacetylenes are prepared from the iodo species via a Pd-catalyzed coupling of trimethylsilylacetylene. The trimethylsilyl group is then removed by incubation with tetrabutylammonium fluoride in anhydrous THF. Combinatorial chemistry supply houses made a variety of these iodinated precursors available, and the coupling reaction is quite general.

Ribonucleoside dialdehyde. An aqueous solution of $NaIO_4$ (24 mmol, 1.5 equiv.) is added to 5'-DMT-uridine (16 mmol) in methanol (1.8 L), and the mixture is incubated at room temperature for 3 hours. The periodate cleavage is monitored by TLC. Following the procedure of Summerton, upon the disappearance of 5'-DMT-uridine, the diphenylacetylene derivative from above (or another with a primary amino group) is added was added to the reaction mixture.

Coupled morpholino derivative. The mixture is incubated at room temperature for an additional 35 minutes. The solids are then removed by filtration, and the filtrate is immediately treated with $NaBH_3CN$ (48 mmol) that is added in 2 portions.

The mixture is then incubated at room temperature with stirring overnight. The methanol is removed under reduced pressure via rotary evaporation to yield a residue, which is twice extracted with $CH_2Cl_2$ over $NaHCO_3$. The organic extracts are concentrated under vacuum to give the product as a foam. Purification by column chromatography (silica, EtOAc) is used to separate isomers. The product is dried under high vacuum at 50° C. for 24 hours.

In alternative procedures, the 5'-DMT-uridine is replaced by the 5'-DMT-derivatives of adenosine, cytidine, guanosine, 2-aminoadenosine, and other non-standard ribonucleosides as well known in the art, with the exocyclic functionalities on the nucleobases protected to make them suitable for solid phase phosphoramidite DNA synthesis.

Preparation of the controlled pore glass. Aminopropylsilylated controlled pore glass that has been reacted with succinic anhydride is used as the support for the DNA synthesis. The morpholino derivative from the previous step (or the corresponding adenosine, guanosine, cytidine, or other ribonucleoside derivative, with their exocyclic functionalities on the nucleobases protected to make them suitable for solid phase phosphoramidite DNA synthesis) were coupled to the support using dicyclohexylcarbodiimide in rigorously anhydrous tetrahydrofuran. The support is washed three times with anhydrous acetonitrile, and used for the synthesis of the 5'-probe fragment using commercially available phosphoramidites for the synthesis of DNA in the (less frequently applied) 3'-to-5' direction. The product is cleaved from the support using aqueous ammonia, following standard procedures.

Example 2

Preparation of the Probe Containing a Photoenolizable Species

Preparation of the 5'-amino-5'-deoxyDNA fragment. DNA having the 5'-terminal nucleotide having its 5'-OH group replaced by a 5'-amino group, and having a sequence complementary to the preselected analyte sequence, is prepared using standard methods. This precursor may even be obtained commercially from oligonucleotide synthesis companies. In the final step before release of the DNA from the solid support, the 5'-amino group is reacted with the isocyanato derivative of the 2-methylbenzophenone derivative whose preparation is described below, or with another 2-methylbenzophenone derivative prepared in an analogous way.

(2'-Methyl)-benzophenone-4-carboxylic acid azide. To a solution of (2'-methyl)benzophenone-4-carboxylic acid (5 mmol) in DMF (25 mL) is added anhydrous diphenylphosphoryl azide (DPPA, 5 mmol) and anhydrous triethylamine (9 mmol). The mixture is incubated for 1 hour at room temperature. The mixture is diluted with EtOAc (350 mL). The organic mixture is washed with a solution of aqueous saturated NaCl (150 mL), and then twice with water (100 mL, 2×). The organic layer is then dried using anhydrous $MgSO_4$. The organic layer is then recovered by filtration and concentrated under vacuum to give the azide, which is used immediately without purification.

4-Isocyanato-(2'-methyl)-benzophenone: About half of the crude acyl azide is dissolved in anhydrous toluene (20 mL). The solution is then heated to reflux until the evolution of dinitrogen is no more visible. The mixture is then allowed to cool to room temperature, the solvents were removed by rotary evaporation under reduced pressure, and the isocyanate is used directly.

Modification of 5'-amino DNA: DNA to serve as the 3'-probe, carrying a 5'-deoxy-5'-amino nucleoside, is prepared by standard solid phase synthesis according to standard protocols. Phosphoramidites, including the 5'-amino nucleoside analog where the 5'-amino group is protected as a 5'-monomethoxytrityl ether, are available from Glen Research. The final detritylation will be done with 2% dichloroacetic acid for 15 min. The product is then treated with the isocyanato derivative in dimethylformamide at 25° C. The products are then purified by standard oligonucleotide HPLC (reversed phase C-18, water-acetonitrile eluant).

REFERENCES

[Ben04] Benner, S. A. (2004) Understanding nucleic acids using synthetic chemistry. *Acc. Chem. Res.* 37, 784-797

[Car88] Cardullo, R. A. et al. (1988) Detection of nucleic acid hybridization by nonradiative fluorescence resonance energy transfer. *Proc. Nat. Acad. Sci. USA* 85, 8790-8794

[Hut02] Hutter, D., Blaettler, M. O., Benner, S. A. (2002) From phosphate to dimethylenesulfone: Non-ionic backbone linkers in DNA. *Helv. Chim. Acta.* 85, 2777-2806

[Kie86] Kiedrowski, G. V. (1986) A self-replicating hexadeoxynucleotide. *Angew. Chem.* 98, 932.

[Tsi93] Tsien, R. Y., Bacskai, B. J., Adams, S. R. (1993) FRET for studying intracellular signalling. *Trends Cell Biol.* 3, 242-245.

[Tsu01] Tsuji, A. et al. (2000) Direct observation of specific messenger RNA in a single living cell under a fluorescence microscope. *Biophys. J.* 78, 3260-3274.

[Tsu01] Tsuji, A. et al. (2001) Development of a time-resolved fluormetric method for observing hybridization in living cells using fluoirescence resonance energy transfer. *Biophys. J.* 81, 501-515.

[Tsu01] Tsuji, A. et al. (2001) Development of a time-resolved fluormetric method for observing hybridization in living cells using fluoirescence resonance energy transfer. *Biophys. J.* 81, 501-515

[Xu97] Xu Y, Kool E T (1997) A novel 5'-iodonucleoside allows efficient nonenzymic ligation of single-stranded and duplex DNAs. *Tetrahedron Lett.* 38, 5595

[Yan61] Yang, N. C., Rivas, C. (1961) A new photochemical primary process. The photochemical enolization of o-substituted benzophenones. *J. Am. Chem. Soc.* 83, 2213-2214

What is claimed is:

1. A process for covalently linking a molecule X-A to a molecule B-Y to give a detectable product molecule X-A-B-Y, wherein all of the bonds between X, A, B, and Y in said product molecule are covalent and moieties A and B do not react with each other spontaneously under the conditions of the process, wherein A is a moiety that upon irradiation with light forms a moiety A* that is not electronically excited, wherein said process comprises (i) contacting X-A and B-Y in a solution comprising solvent S with a preselected nucleic acid molecule N under conditions where X-A and B-Y bind to adjacent segments of N, wherein said binding brings moieties A and B into proximity, (ii) irradiating said solution with light having a wavelength that converts A into A* and (iii) the reaction of said A* with moiety B to form a covalent bond between at least one atom in A and at least one atom in B, wherein A is selected from the group consisting of a photoenolizable ketone, a cyclic lactone, a phosphoramidite, and an azide.

2. The process of claim 1 wherein said solvent S is water.

3. The process of claim 1 wherein said solvent S is formamide mixed with water.

4. The process of claim 1 wherein the A-B moiety in said product molecule is fluorescent.

5. The process of claim 1 wherein said product molecule dissociates from the preselected nucleic acid molecule N following the process.

6. The process of claim 1 wherein said product molecule is fluorescent and said product molecule dissociates from the preselected nucleic acid molecule N under the conditions of the process.

7. The process of claim 1 wherein said product molecule serves as a template for a DNA or RNA polymerase.

8. The process of claim 1 wherein said product molecule is fluorescent and said product molecule does not dissociate from the preselected nucleic acid molecule N under the conditions of the process.

9. The process of claim 1 wherein A* spontaneously reverts to A if it does not encounter B.

10. The process of claim 1 wherein said moieties X and Y are oligonucleotides or oligonucleotide analogs.

11. The process of claim 1 wherein said moieties X and Y bind to said nucleic acid molecule N according to Watson-Crick pairing, wherein adenosine in a moiety pairs with thymidine in N, thymidine in a moiety pairs with adenosine in N, cytidine in a moiety pairs with guanosine in N, and guanosine in a moiety pairs with cytidine in N.

12. The process of claim 1 wherein said irradiation converts an azide that is comprised by the A moiety into a nitrene that is comprised by the A* moiety.

13. The process of claim 1 wherein said irradiation converts the A moiety by a photoextrusion reaction into the A* moiety, said A* moiety comprising a 1,3-diene.

14. The process of claim 1 wherein said irradiation converts the A moiety by a photoenolization reaction into the A* moiety, said A* moiety comprising a 1,3-diene.

15. The process of claim 1 wherein said irradiation converts the A moiety that comprises a protected phosphoramidite into the A* moiety, said A* moiety comprising a phosphorothioate nucleophile.

16. The process of claim 1 wherein said detectable product molecule comprises a substituted naphthalene derivative.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cttcaggtac tgagtcaagc                                            20
```

-continued

```
<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gcttgactca gtacctgaag                                                   20

<210> SEQ ID NO 3
<211> LENGTH: 20
<212> TYPE: RNA
<213> ORGANISM: Artificial Sequence
<220> FEATURE:
<223> OTHER INFORMATION: Synthetic

<400> SEQUENCE: 3
cuucagguac ugagucaagc                                                   20

<210> SEQ ID NO 4
<211> LENGTH: 20
<212> TYPE: RNA
<213> ORGANISM: Artificial Sequence
<220> FEATURE:
<223> OTHER INFORMATION: Synthetic

<400> SEQUENCE: 4
gcuugacuca guaccugaag                                                   20
```